United States Patent [19]
Cookston et al.

[11] Patent Number: 6,132,390
[45] Date of Patent: Oct. 17, 2000

[54] HANDLE FOR MANIPULATION OF A STYLET USED FOR DEFLECTING A TIP OF A LEAD OR CATHETER

[75] Inventors: H. Stephen Cookston, Brentwood; Eli Gang, Los Angeles, both of Calif.; John Wright, Lino Lakes, Minn.

[73] Assignee: Eupalamus LLC, Brentwood, Calif.

[21] Appl. No.: 09/175,164

[22] Filed: Oct. 19, 1998

Related U.S. Application Data

[63] Continuation-in-part of application No. 08/608,557, Feb. 28, 1996, Pat. No. 5,824,031.

[51] Int. Cl.[7] .................................................. A61N 1/05
[52] U.S. Cl. .......................................... 600/585; 607/122
[58] Field of Search ................................ 607/119, 122, 607/585

[56] References Cited

U.S. PATENT DOCUMENTS

| | | | |
|---|---|---|---|
| 4,757,827 | 7/1988 | Buchbinder et al. | 600/585 |
| 5,254,088 | 10/1993 | Lundquist et al. | 600/585 |
| 5,376,109 | 12/1994 | Lindegren et al. | 607/122 |
| 5,396,902 | 3/1995 | Brennen et al. | |
| 5,439,006 | 8/1995 | Brennen et al. | |
| 5,662,119 | 9/1997 | Brennen et al. | |
| 5,882,333 | 3/1999 | Schaer et al. | 600/585 |
| 5,895,416 | 4/1999 | Barreras, Sr. et al. | |
| 5,997,487 | 12/1999 | Kolehmainen et al. | |

*Primary Examiner*—Carl H. Layno
*Attorney, Agent, or Firm*—Daniel L. Dawes

[57] ABSTRACT

A deflectable stylet is comprised of a hollow tube with a reduced diameter distal portion including a semi-cylindrical ground portion to provide localized flexure wherein tension is applied to an axial tension wire fixed to the distal end of the hollow tube. The hollow tube is coupled to a rotationally fixed tip coupled to a rotationally fixed handle body. The handle body and the tip are telescoped longitudinally with respect to each other along the longitudinal axis of the hollow tube by means of a rotatable nut that advances out of or backs the handle into the tip. The tension wire is coupled to the handle body so that when the nut is rotated in a first direction and the handle body backed out, tension is applied to the wire which is then withdrawn from the hollow tube fixed to the tip causing the stylet to curve at its distal end. Rotation of the nut in the opposite direction reduces the tension on the wire causing the stylet to straighten at its distal end. By this means fine, micrometer adjustments of the curvature of the stylet are reliably and repeatedly made. A conical tip of the handle is coupled to the catheter and provides stress relief to the stylet. The tip is freely rotatable with respect to the handle, but can be locked to the terminal pin of the catheter so that an active fixation pacemaker lead is activatable by rotation of the tip.

21 Claims, 7 Drawing Sheets

HANDLE FOR MANIPULATION OF A STYLET USED FOR DEFLECTING A TIP OF A LEAD OR CATHETER

RELATED APPLICATIONS

This application is a continuation in part of U.S. patent application Ser. No. 08/608,557, filed Feb. 28, 1996, now issued as U.S. Pat. 5,824,031.

BACKGROUND OF THE INVENTION

1. Field of the Invention

The invention relates to the field of cardiac leads and catheters, including pacemaker leads, defibrillator leads, ablation leads, mapping leads and the like, and in particular, to an apparatus and method for variably and controllably changing the curvature of the tip of such a cardiac lead.

2. Description of the Prior Art

Currently, during the implantation of a permanent cardiac pacemaker system, the leads are introduced into a vein either via a cut down or percutaneous sheath introduction and are positioned under fluoroscopy into either the right atrium, right ventricle, or both in the case of a dual chamber pacing system. The positioning of the pacemaker leads is the most time consuming and difficult aspect of the implantation. The current practice for lead placement requires the surgeon or cardiologist to advance the cardiac lead toward the heart through the veins until initial access is obtained. As the lead passes through the tributary veins into the subclavian vein and then into the right atrium of the heart, a straight stylet or wire must be disposed within a longitudinal lumen within the cardiac lead in order to give the lead sufficient strength and rigidity to proceed into the right atrium. An important aspect of proper placement is crossing of the tricuspid valve. In order to achieve this, the straight stylet is withdrawn and the physician fashions a curve at the tip of another stylet. Thereafter, most physicians continue advancing the lead with the curved tip stylet in place into the pulmonary artery outflow tract to confirm right ventricle access and to rule out the possibility of entrance into the coronary sinus or coronary vein, which can mimic the appearance of a right ventricle placement under fluoroscopy. Once the physician has confirmed that placement of the lead is in fact in the pulmonary outflow tract, the conventional practice requires the physician to then remove the curved stylet and partially readvance the original or another straight stylet into the lead. The cardiac lead is then carefully pulled back under direct fluoroscopic observation until the lead drops from the proximal portion of the pulmonary artery to the floor of the right ventricle, after which the physician advances the stylet to its fully advanced position within the lead to advance the lead to the distal most portion of the right ventricular apex.

In the case of atrial lead placement, the lead is then positioned into either the right atrial appendage or is fixed by means of an active fixation screw or tines into or near the septum or other portion of the atrium selected by the physician.

In the case where a ventricular lead is being implanted, the lead must be passed from the right atrium into the right ventricle through the tricuspid valve. Due the anatomy of the right ventricle, it is necessary to remove the straight stylet and then introduce a curved tip stylet, which the physician fashions manually from a standard straight stylet, so that the lead will have an appropriate shape, turn appropriately and pass through the tricuspid valve.

In the case where the lead does not have a screw fixation and is passive or has tines on the lead tip, the lead is then left in a visually appropriate position as determined by fluoroscopy and electrical testing is performed to confirm proper electrical contact. In the case of an active fixation lead, namely one having a screw-in-type tip, the attachment mechanism is then activated to secure the distal tip of the pacing lead into the endocardium at the selected position.

In a typical pacemaker implantation therefor, there are multiple exchanges of straight stylets and curved stylets which have been bent according to the physician's choice. The stylet is a thin solid wire, typically of about 0.014–0.018 inch in diameter. During handing, they can easily become bent or kinked, and thereafter cause great difficulty when an attempt is made to reinsert them through the narrow inner diameter of the lead's lumen, which may only be 0.019 inch in the case of a stylet of 0.018 inch or less diameter, typically providing no more than 0.0005 inch clearance on each side.

In addition, because the surgeon is working through an open wound, even the most fastidious surgeon will have blood on his gloves which will be transferred to the stylet. The blood congeals, and because of the small clearance, even a few drops of blood is sufficient to causing jamming of the stylet inside the lead body. When the stylet jams in the lead body, kinking of the stylet within the lead can occur, which kinks, in turn, will create new jams or problems with the insertion and retraction of the stylet from the lead.

The overall result of such difficulties is that operative time is greatly increased which results in much higher X-ray exposures to the patient, who is under continuos fluoroscopy, including scattered X-ray exposure to the operating room staff, increased cost due to procedural time delays, and in some cases, the jamming is so severe that the cardiac lead must be removed from the heart for fear of insulation puncture, discarded and a new lead implanted, thereby at least doubling the lead cost used in the procedure as well as operative time.

Therefore, what is needed is some type of apparatus or method that eliminates the need for any stylet removal or hand fashioning of a curve in a stylet by the physician, and which therefore will dramatically shorten X-ray risks to the patient and to the staff. The method should dramatically reduce the total time of operation for a pacemaker implantation, thereby broadly reducing the cost of this procedure under national and private health care cost schedules.

The same methodology is used in placing transvenous defibrillating leads which, in essence, are large pacing leads positioned at the apex of the right ventricle.

The apparatus and method should be such that it is usable in both pediatric and adult patients with considerably different sized heart structures.

The apparatus and methodology should be applicable to any type of cardiac implantation used, including the atrial and ventricular placements with both passive and active fixation and any type of device that utilizes a lead or catheter.

BRIEF SUMMARY OF THE INVENTION

The invention is a handle for use with a deflectable stylet for disposition into a catheter. The handle comprises a non-rotational handle body, and a rotatable adjustment coupled to the handle body. The handle body is coupled to the deflectable stylet and adapted to apply a tension thereto to cause the stylet to deflect according to the degree of rotation of the adjustment relative to the non-rotational handle body.

In one embodiment the catheter has a terminal pin. The handle body is further combined with a rotatable tip. The stylet is disposed through the tip such that the stylet is coupled to and rotationally fixed with respect to the handle body. The tip is rotationally free with respect to the handle body and is selectively rotationally fixed to the terminal pin of the catheter.

The rotatable adjustment is a nut threadably coupled to the handle body. The tip is coupled to and captured by a rotationally free engagement with the handle body.

In the illustrated embodiment the stylet is comprised of a hollow tube and tension wire coupled to the hollow tube. The hollow tube is fixed to a keyed sleeve. The keyed sleeve is longitudinally slideable in and keyed to the handle body so that it is rotationally fixed thereto. The keyed sleeve has a longitudinal mechanical stop. The wire is fixed with respect to the handle body. The keyed sleeve is resiliently biased relative to the handle body to apply a tension to the tension wire. The handle further comprises a screw adjustment. The screw adjustment adjusts the relative longitudinal displacement of the keyed sleeve to the handle body to add tension to the wire. The handle further comprises a slide block forming part of the screw adjustment. The tension wire has its distal end fixed to the slide block. The slide block is longitudinally positionable within the handle body by the screw adjustment.

The handle further comprises an attachment ring connected to the handle body to permit fixation of the handle with a field of operation.

The handle is used in combination with a deflectable stylet, which comprises a hollow tube having a distal end and a proximal end coupled to the handle. The hollow tube has a central coaxial tension wire disposed therein and fixed thereto at the distal end of the tube. The distal tip of the hollow tube has a reduced diameter section. A portion of the reduced diameter section is removed to form a flexure section. A flexible hollow cylindrical jacket is concentrically disposed over the reduced diameter section of the hollow tube. The hollow tube has an outer diameter and the flexible jacket is plastic tubing having an inner diameter adapted to snugly fit over the reduced diameter section and an outer diameter comparable to the outer diameter of the hollow tube.

The invention is also defined as a handle for use with a deflectable stylet disposable within a lumen in a catheter. The stylet and catheter is curved upon application of tension to a tension wire which is disposed in the stylet and extends from its proximal end to its distal end wherein the tension wire is fixed. The handle comprises a non-rotatable body adapted to be held by a user, and a screw micrometer telescopic adjustment for moving the body longitudinally relative to the catheter. The body is coupled to the tension wire so that the tension wire is drawn out of the deflectable stylet and tension applied to the tension wire to thereby curve the stylet and hence to curve the catheter.

The telescopic adjustment is a rotatable collar which longitudinally displaces a first portion of the body coupled to the tension wire from a second portion of the body coupled to the stylet.

The handle further comprises a keyed sleeve coupled to the stylet and which is rotationally fixed but slideable in the first portion of the body coupled to the tension wire so that the first and second portions of the body are rotationally fixed with respect to each other, while remaining longitudinally displaceable by action of the telescopic adjustment. The handle further comprises a stop to prevent longitudinal displacement of the first and second portions of the body beyond a predetermined distance. The stop prevents curvature of the distal portion of the stylet beyond a predetermined flexure. The telescopic adjustment is performed by means of rotation of a tensioning member which translates rotation of the member into tension on the wire. The telescopic adjustment is by means of rotation of screw micrometer which reversibly tensions the wire.

The handle further comprises a screw adjustment to add tension to the wire after the stop has been first actuated.

The handle further comprises a tip. The stylet is disposed through a lumen in the tip. The catheter is coupled to the tip so that the tip provides stress relief to the stylet when the handle is coupled to the catheter.

The tip is longitudinally coupled to the body, but rotationally free with respect to the body. In the case where the catheter is an active fixation pacemaker lead, it has a terminal pin which is engaged by a screw lock disposed in the tip to lock the terminal pin so that the terminal pin rotates with the tip to activate fixation of the catheter.

The invention can be better visualized by now turning to the following drawings, wherein like elements are referenced by like numerals.

BRIEF DESCRIPTION OF THE DRAWINGS

FIG. 2 is a simplified longitudinal cross section of the tip or distal portion of the instrument shown in FIG. 1a.

These and other embodiments or implementations of the invention may be better understood by now turning to the following detailed description.

DETAILED DESCRIPTION OF THE PREFERRED EMBODIMENTS

A deflectable stylet is comprised of a hollow tube with a reduced diameter distal portion including a semi-cylindrical ground portion to provide localized flexure wherein tension is applied to an axial tension wire fixed to the distal end of the hollow tube. The hollow tube is coupled to a rotationally fixed tip coupled to a rotationally fixed handle body. The handle body and the tip are telescoped longitudinally with respect to each other along the longitudinal axis of the hollow tube by means of a rotatable nut that advances out of or backs the handle into the tip. The tension wire is coupled to the handle body so that when the nut is rotated in a first direction and the handle body backed out, tension is applied to the wire which is then withdrawn from the hollow tube fixed to the tip causing the stylet to curve at its distal end. Rotation of the nut in the opposite direction reduces the tension on the wire causing the stylet to straighten at its distal end. By this means fine, micrometer adjustments of the curvature of the stylet are reliably and repeatedly made. A conical tip of the handle is coupled to the catheter and provides stress relief to the stylet. The tip is freely rotatable with respect to the handle, but can be locked to the terminal pin of the catheter so that an active fixation pacemaker lead is activatable by rotation of the tip.

Figure 1A:
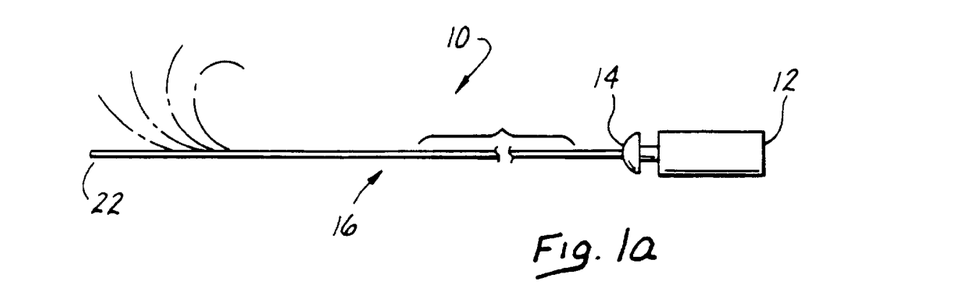
FIG. 1a is a block diagram illustrating the first embodiment of the invention in which a segmented terminal pin is utilized to manipulate a pull wire for providing a tip curvature of the instrument.
Figure 1B:
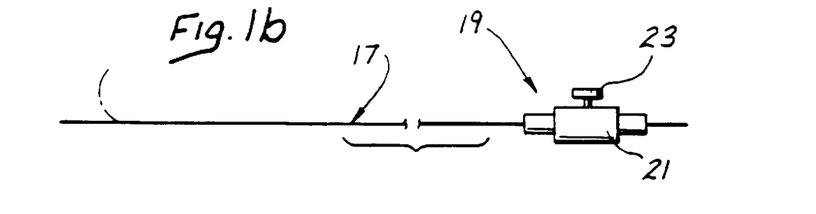
FIG. 1b is a block diagram illustrating a curvable or steerable stylet in isolation of the instrument into which it is inserted.
Figure 2:
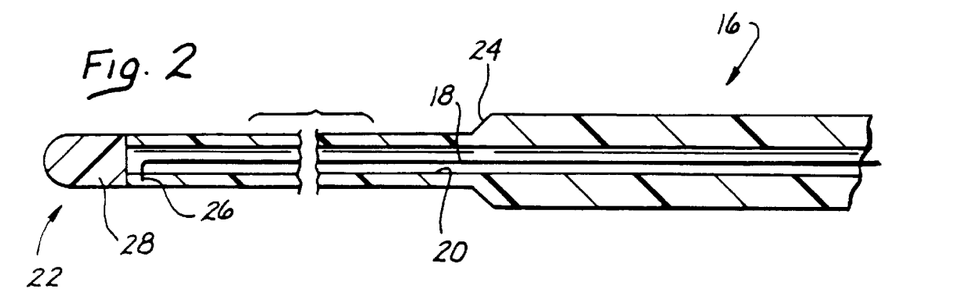
Figure 3:
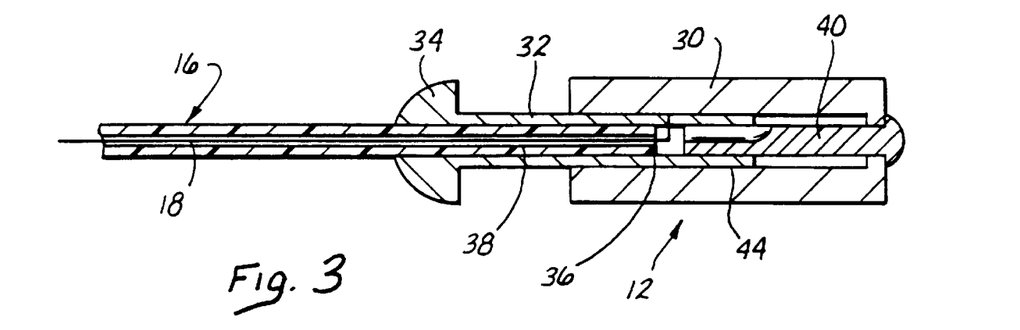
FIG. 3 is a simplified longitudinal cross section showing the proximal portion of the instrument in FIG. 1a, and in particular, the connection of the pull wire to the terminal pin.
Figure 7:
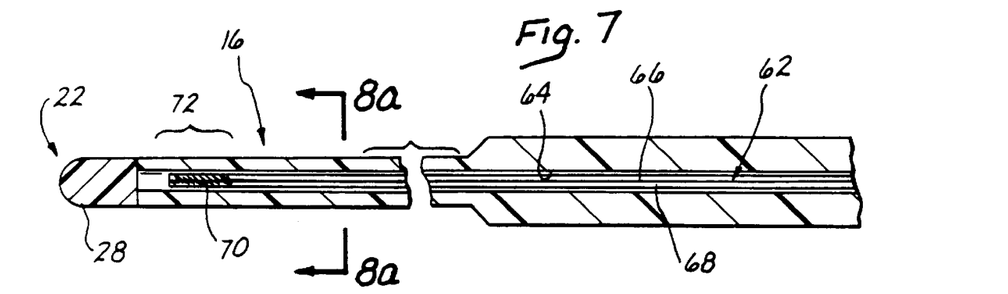
FIG. 7 is a simplified longitudinal cross sectional view of the distal tip of another embodiment of a instrument wherein a differential pull wire is utilized to impart a curvature to the tip.
Figure 8A:
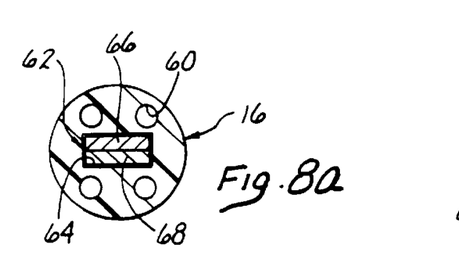
FIG. 8a is perpendicular cross sectional view of the distal tip shown in the FIG. 7 as seen through section lines 8—8 of FIG. 7.
Figure 8B:
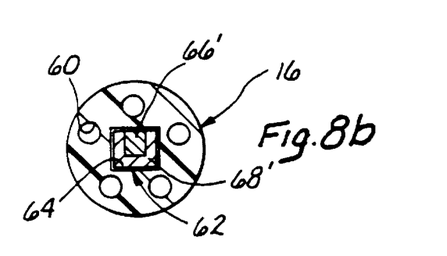
FIG. 8b is perpendicular cross sectional view of the distal tip similar to that shown in the FIG. 7 as seen through section lines 8a—8a of FIG. 7, wherein the cross section of the stylet has been modified to comprise a rectangular wire disposed in a U-shaped wire.
Figure 9:
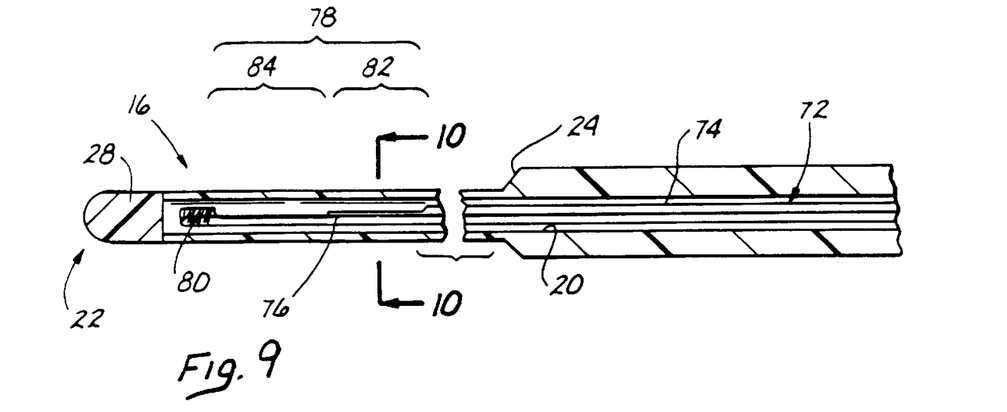
FIG. 9 is a longitudinal cross-sectional view of another implementation of the pull wire technique equivalent to what is generally described in connection with the system of FIG. 1.
Figure 10:
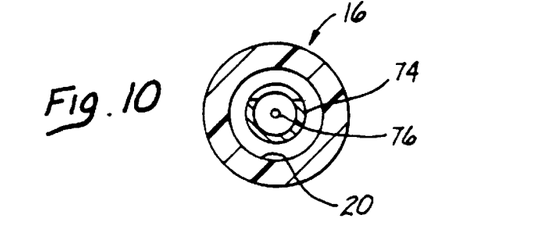
FIG. 10 is a perpendicular cross sectional view of the distal tip of FIG. 9 as seen through section lines 10—10 of FIG. 9.

The distal tip of the cardiac instrument may be variably and controllably curved by integrating a steering mechanism into the instrument construction itself as is in the case of the embodiment of FIGS. 1a, 2 and 3 or in a stylet which is inserted into a lumen within the instrument as is in the case with the embodiments of FIGS. 1b, 4–8, and 11–14 and the example of FIGS. 9 and 10. Therefore, it must be expressly understood that while only certain mechanisms for providing controllable curves in the distal tip are illustrated in the specification, any mechanism capable of providing the controlled curvature, including those beyond those specifically illustrated, is contained within the scope of the invention.

In one embodiment the deflectable stylet is comprised of a hollow tube with a reduced diameter distal portion including a semi-cylindrical ground portion to provide localized flexure wherein tension is applied to an axial tension wire fixed to the distal end of the hollow tube. The hollow tube is coupled to a rotationally fixed tip coupled to a rotationally fixed handle body. The handle body and the tip are telescoped longitudinally with respect to each other along the longitudinal axis of the hollow tube by means of a rotatable nut that advances out of or backs the handle into the tip. The tension wire is coupled to the handle body so that when the nut is rotated in a first direction and the handle body backed out, tension is applied to the wire which is then withdrawn from the hollow tube fixed to the tip causing the stylet to curve at its distal end. Rotation of the nut in the opposite direction reduces the tension on the wire causing the stylet to straighten at its distal end. By this means fine, micrometer adjustments of the curvature of the stylet are reliably and repeatedly made.

Turn first to the embodiment of FIG. 1a wherein the lead system, generally denoted by reference numeral 10, is diagrammatically depicted as being comprised of a segmented terminal pin 12 connected at the proximal end 14 of instrument 16. Terminal pin 12 is attached, for example, to a pull wire 18 best depicted in FIGS. 2 and 3, which is disposed in a longitudinally defined lumen 20 along the length of instrument 16 extending from its distal tip 22 to its proximal end 14. By drawing in or providing a tension on pull wire 18 as will be described in greater detail in connection with FIGS. 2 and 3, distal tip 22 of instrument 16 is drawn up or curved backwardly toward proximal end 14 as shown in dotted outline in FIG. 1a. Otherwise, the normal or relaxed configuration of instrument 16 is undeflected or straight as shown in solid outline in FIG. 1a. At the proximal end of the instrument is a terminal pin, a segment of which manipulates the distal tips flexion and the instruments overall column strength. When the terminal pin segment is rotated clockwise, for example, the instrument tip assumes a J-shaped contour, suitable for passage through the tricuspid valve, into the pulmonary outflow tract, and into the right ventricle or atrial appendage. When the terminal pin is rotated counterclockwise, the instrument body becomes rigid, suitable for wedging the instrument or to perform instrument retraction in the event that it is required. Bringing the terminal pin to a center or neutral position, turns the tip to a straight nonrigid state.

FIG. 1b is a simplified abstract diagram illustrating a curvable or steerable stylet which may be used in the instrument of FIG. 1a. Stylet 17 is coupled at its proximal end 19 to a manipulatable handle 21, which by the various means discussed below includes a pushable, turnable, or selectively activatable element 23 which when selected causes at least the tip or other portion of stylet 17 to curve if straight or to straighten if curved.

In alternative embodiments, a J-curve may be prebiased within instrument 16 and advancement of wire 18 within its corresponding lumen 20 used to straighten distal tip 22. In this case pull wire 18 is actually more accurately referred to as a push wire. In the following the context of the description will make it clear whether a tension or compression is being applied to wire 18. In general the wire may be either pushed or pulled as needed. The instrument is supplied with a prebiased curve and when the terminal pin is rotated, the instrument becomes straight. Continuous deflections are possible between the straight and maximum curved position according to the user selection.

Consider the pull wire 18 in the embodiment of FIGS. 2 and 3. Distal tip 22 or instrument 16 is typically highly flexible and has a thinned diameter as compared to the more proximal portions of instrument 16 as provided by the narrowing of shoulders 24 shown in FIG. 2. Pull wire 18 is mechanically or adhesively fixed at point 26 near distal tip 22, such as immediately behind tip electrode 28. Tension applied on pull wire 18, drawing wire 18 back within its lumen 20, will therefore cause tip 22 to curve back toward the proximal end 14 as shown in FIG. 1a by varying degrees depending on the amount of tension and retraction applied to wire 18.

One means for providing the retractile force on wire 18 is shown in detail in terminal pin 12 of FIG. 3 which depicts a simplified longitudinal cross section of terminal pin 12. Terminal pin 12 is comprised of a body 30 which provides the primary hand-hold for the surgeon. A retractable piston 32, having a distal knob 34 to facilitate in its longitudinal displacement within cylindrical body 30, slip fits or is otherwise longitudinally displaceable within body 30. While piston 32 is easily movable within body 30 under manual pressure, the degree of friction or engagement between piston 32 and body 30 is such that the reactive tension of wire 18 created by the curvature of distal tip 22 is nevertheless insufficient to move piston 32 relative to body 30 once the physician has made an adjustment between them.

For example, wire 18 extends within instrument 16 and exits its proximal end 36 to be fixed, adhered or otherwise connected to piston 32. Likewise, instrument 16 is itself loosely disposed with an axial longitudinal bore 38 defined through piston 32 so that there is little, if any, frictional engagement between piston 32 and the outside surface of instrument 16. Meanwhile, a stop rod 40 having an axial longitudinal slot is connected to body 30, such as being screwed through its end wall 42, which stop rod extends into the longitudinal bore 38 of piston 32 to provide an abutting interference stop to proximal end 36 of instrument 16. However, longitudinal slot defined in rod 40 allows wire 18 to be disposed through the slot as piston 32 is pushed to the left in FIG. 3 thereby drawing wire 18 out of instrument 16.

It is to be expressly understood that terminal pin 12 is shown in only one embodiment and that many other types of structures may be employed for pulling or pushing wire 18 within its longitudinal lumen 20 of instrument 16. For example, instead of the telescopically slideable piston assembly of FIG. 3, piston 32 could be provided with external threading for threadable coupling to bore 44 of body 30. In this instance, a swivel connection through a washer or the like could be provided for the coupling between wire 18 and rotatable threaded piston 32 so that wire 18 is advanced or retracted by screwing piston 32 in or out of body 30.

Figure 4:
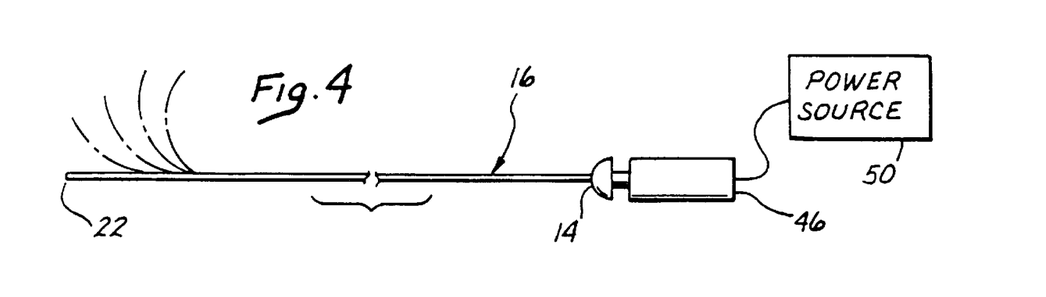
FIG. 4 is a simplified block diagram showing a second embodiment of the invention in which a stylet is utilized in the instrument and is thermoelectrically curved to control tip curvature of the instrument.
Figure 5:
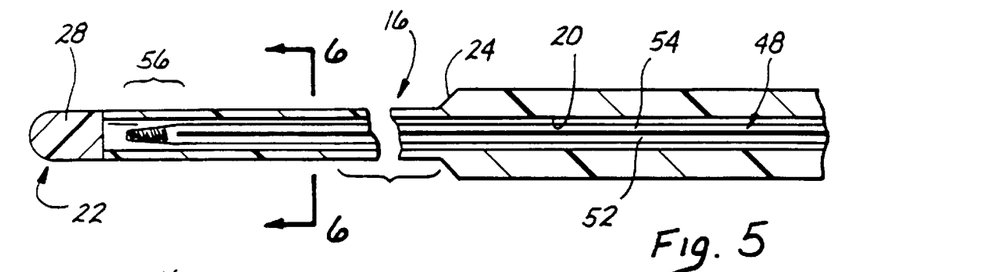
FIG. 5 is a simplified longitudinal cross sectional view of the distal portion of a instrument usable in the system of FIG. 4.
Figure 6:
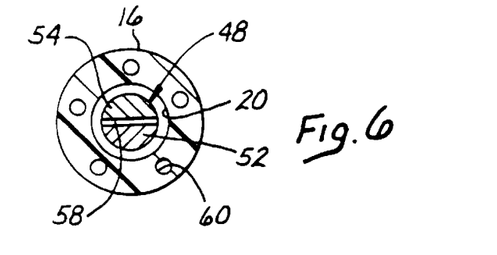
FIG. 6 is a perpendicular cross sectional view of the tip shown in FIG. 5 as seen through section line 6—6 of FIG. 5.

Another embodiment of the invention is depicted in FIG. 4 wherein a thermoelectrically curvable stylet as describe in connection with FIGS. 5 and 6 is utilized to impart the distal tip curvature to instrument 16. In the embodiment of FIG. 4, terminal pin 12 is replaced by a handle and electrical connector 46, which is connected to the proximal end of stylet 48 disposed within lumen 20 of instrument 16. Handle and connector 46 are then electrically coupled to a power source 50 which provides an appropriate voltage and current for heating the differential elements of stylet 48 to achieve the acquired curvature for the predetermined time.

Turning specifically to FIGS. 5 and 6, stylet 48 is shown as being comprised at least on part of its distal portion of a first strip 52 disposed adjacent to a second strip 54. Strips 52 and 54 are preferably made of different metals and electrically insulated from each other along their length except for distal portion 56 where they are electrically and physically coupled together. Current flows through one strip 52 through their electrical coupling at distal portion 56 and thence back to power source 50 through strip 54. Ohmic heating occurring in strips 52 and 54 cause the two materials to expand or contract at different rates, thereby creating an asymmetric tension along their length which in turn causes stylet 48 to curve if originally in the straight unbiased configuration or to uncoil if in an originally curved configuration and if the more thermally expansive strip 52 or 54 disposed on the inside of the curve much like a conventional bimetallic strip.

For example, a stylet of approximate 0.014 to 0.018 inch in outer diameter and in lengths varying from 40 to 60 centimeters is provided in which the proximal end of the stylet has a manipulation handle attached to a power source which is battery operated or line powered. The stylet is made of Nitinol, either alone or in combination with other materials. When the power source is activated, the tip of the stylet is deflected and assumes a curved contour suitable for manipulation through the tricuspid valve and into the pulmonary outflow tract. When the power source if switched off, the tip returns to a straight configuration.

In another embodiment, the instrument is supplied in a prebiased curve form and when the power source is applied, it straightens. The degree of deflection between straight and the most curved position is continuous so that the degree of curvature is arbitrarily selected by the user.

It also must be understood that stylet 48 need not include the bithermal or bimetallic strip pair 52 and 54 along its entire length. Instead, the bimetallic portion may only be in the proximity of distal tip 22 with the remaining portion being a single wire. The two portions would then be in electrical contact with each other and the circuit completed by return wire connected at the distal end of the bimetallic strip and returning to current source 50.

The perpendicular cross section of stylet 48 is depicted in FIG. 6 as seen through section line 6—6 of distal tip 22. In the illustrated embodiment, strip portions 52 and 54 are shown as substantially in the form of half cylinders joined on their common diameter, either by an insulating layer 58, or conductive solder or other conductive layer in place of layer 58 depending upon whether strips 52 and 54 are utilized in the same portion of the circuitry in parallel or are serially connected as described above.

Furthermore, in both the embodiments of FIGS. 1–3 and 4–6, pull wire 18 or stylet 48 has been shown as being disposed in a central or axial lumen 20 of instrument 16. This need not be the case and other lumen cross sectional shapes and positions may be equivalently employed. For example, as will be described below in connection with the embodiment of FIGS. 7 and 8, the lumen may have a noncircular perpendicular cross section to provide for angular fixation of pull wire 18 or stylet 48 within instrument 16 or may be positioned in an off axis lumen 60 defined within the wall thickness of instrument 16. Typically, multiple lumens are defined through the longitudinal length of instrument 16 for providing one or more electrical circuits to electrodes included on the instrument, such as tip electrode 28, or other sensing, ablation or defibrillation electrodes, which may be placed along its length.

Consider another example of the invention as shown in FIGS. 7 and 8a in which stylet 48 of the embodiment of FIGS. 5 and 6 are replaced by a stylet 62 disposed within a rectangular or square lumen 64 defined within instrument 16. Stylet 62 in this case is comprised of two pull wires 66 and 68. Pull wires 66 and 68 are shown in the perpendicular cross section of FIG. 8a as seen through section lines 8a—8a of FIG. 7 as being rectangular in cross section and therefore comprise two longitudinal strips sandwiched together. Flat wire 66 and 68 may be fixed together at their distal end by soldering, crimping, adhering or any other means as symbolically denoted by coupling 70, which extends along the distal tip of stylet 62 for a predetermined distance 72. When one wire 66 or 68 is pushed or retracted with respect to the other by an appropriate handle mechanism at proximal end 14 of instrument 16, the resulting differential tension will cause the distal tip of stylet 62 to curve. The polygonal cross section of lumen 64 and the conforming cross section of stylet 62 prevents twisting of stylet 62, although cylindrical cross sections could be employed in applications where twisting is not a consideration or does not occur. A predefined degree of clearance between lumen 64 and the exterior envelope of stylet 62 permits the slight bowing of one wire 66 with respect to the other 68 or vise versa, to allow for the curving of stylet 62.

FIG. 8b is a perpendicular cross-sectional view of the stylet of FIG. 7 wherein the perpendicular cross-sectional shape of wires 66 and 68 have been modified from flattened rectangular shapes to a U-shape extrusion for wire 68' and a rectangular solid wire 66' which is disposed in and slides in the channel defined in U-shaped wire 68'.

Alternatively, while the above illustrated embodiment has been implicitly described in terms of nonextensible wires 66 and 68, it is also within the scope of the invention that wires 66 and 68 may be elastomeric, that is either stretchable or compressible. In this case, like the bimetallic coupling described in connection with FIGS. 5 and 6, one wire will compressed or stretched compared to the other, causing a differential tension across their interface, and hence, the curvature of stylet 62.

Therefore, it should be clear that any mechanism which can impress a curve into a stylet inserted into an elongated instrument, be it a lead or catheter, falls within the scope of the invention. Another example by which the invention may be implemented is shown in FIGS. 9 and 10. Again, FIG. 9 is a simplified longitudinal cross sectional view of distal portion 22 of instrument 16. In this example, stylet 72 is disposed within lumen 20 of instrument 16 as before, but is comprised of a resilient or flexible metal tube or cylinder 74, such as a helical spring in which a pull wire 76 has been coaxially disposed. Cylinder 74 is a hollow spring, typically of 0.014–0.018 inch in diameter. Pull wire 76 is a solid thinner wire coaxially disposed within a lumen 28 defined within cylinder 74 and fixed at or near distal end 80 of stylet 72. Tension applied to pull wire 76 will thus cause at least distal portion 78 to curve substantially in the same manner as described above in connection with the embodiments of FIGS. 1–8.

Figure 11:
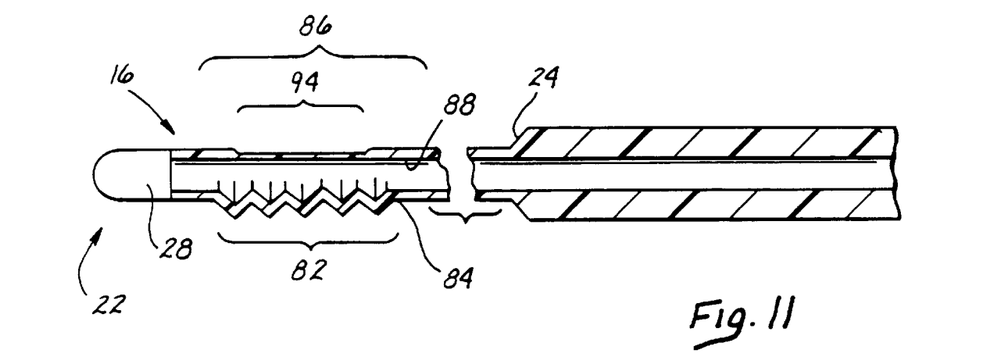
FIG. 11 is a simplified longitudinal cross sectional view of the distal portion of a instrument according to the invention.

In another embodiment, such as shown in FIG. 11, instrument 16 is provided with a portion 82 in which the wall 84 of instrument 16 is defined with an accordion or wrinkled skin. The degree of wrinkling is molded in and extends around the cross section of instrument 16 by predetermined amount, such as approximately halfway around the circumference, so that the opposing portion 86 of wall 84 of instrument 16 is substantially smooth or unwrinkled. Air or fluid pressure then injected, or even simply a push wire inserted, into lumen 88 will cause portion 82 to unfold while the opposing portion 86 remains taut and comparatively nonextendable. This will cause a distal portion of instrument 16 to curve away from wrinkled portion 82. Removal of the pressure allows instrument 16 to resume its nonextended configuration, namely it allows the accordion folds or wrinkles in portion 82 to return to their original configuration due to the resiliency of the material of which instrument 16 is made, thereby straightening the distal portion of instrument 16. Straightening is urged both by the compression of material comprising smooth portion 86 as well as the tension of resilient material comprising portion 82.

Figure 12:
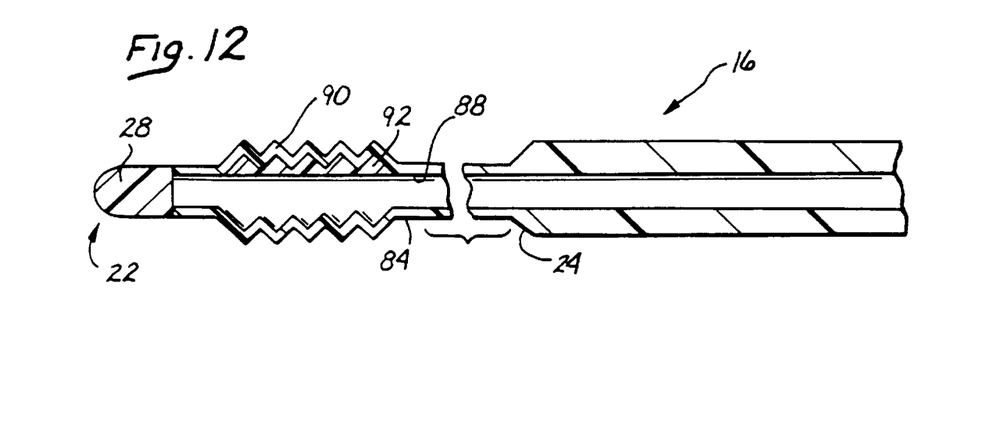
FIG. 12 is a simplified longitudinal cross sectional view of the distal portion of another instrument according to the invention.

The differential expandability of opposing wall portions of instrument 16 may be achieved by other equivalent means such as depicted diagrammatically in FIG. 12 wherein an entire cylindrical segment of wall 84 of instrument 16 has been shaped in the form of an accordion, like a flexible straw or hose. However, one side of the accordion envelope 90 has been interiorly filled with a comparatively nonextensible adhesive 92 to achieve a differential tension when lumen 88 is inflated by pressurized fluid.

The embodiments of FIGS. 11 and 12 have the advantage that lumen 88 can be pressurized to a first level which renders a highly flexible instrument rigid, but without substantially expanding the pleated or accordion section of the distal portion. As the pressure increases to a second higher level, the pleated or accordion portion 82 or 90 is then unfolded with resulting curvature.

Figure 13:
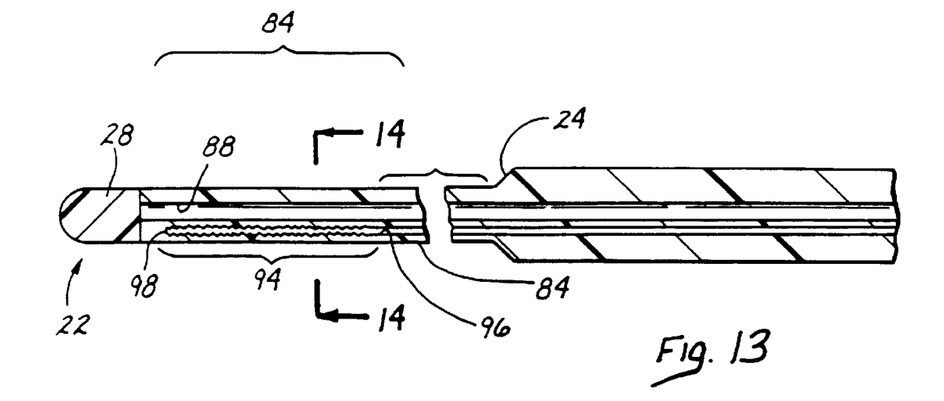
FIG. 13 is a simplified longitudinal cross sectional view of the distal portion of yet another instrument according to the invention.
Figure 14:
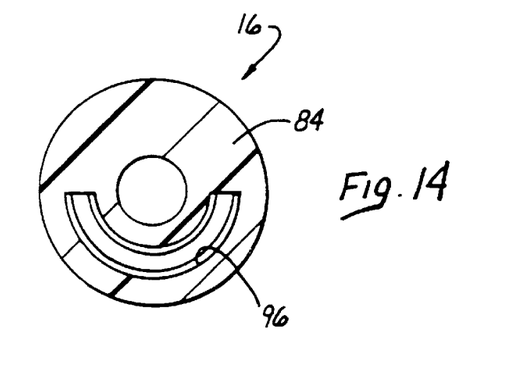
FIG. 14 is a perpendicular cross sectional view of the distal tip of FIG. 13 as seen through section lines 14—14 of FIG. 13.

Opposing wall 84 in portion 86 may be thinned at a predetermined section 94 to assist in the ease of bending and definition of the curvature of the distal portion of instrument 16. In fact, the pleated or accordion portion 82 or 90 may be greatly exaggerated in the form of a bellows to achieve acute bends and define points of bend along the length of instrument 16. In the case where pleating or wrinkling of the exterior surface of instrument 16 cannot be tolerated, the wrinkling or pleating may be entirely formed interiorly within lumen 88 and the exterior of instrument 16 provided at that section with a smooth highly extensible thin skin. For example, as shown in FIG. 13, distal portion 94 of instrument 16 is provided with an off-axis lateral lumen 96 defined within wall 84 along distal portion 94. The interior surface of lumen 96 in distal portion 94 is wrinkled or pleated so that when pressurized by fluid, the extensible material of which wall 84 is comprised, tends to extend longitudinally along the axis of lumen 96 in opposition to the comparatively nonextendable portion of the opposite side of wall 84 thereby resulting in a curvature of the distal tip.

Alternatively, instead of pressurizing lumen 96, a push wire or stylet (not depicted) may be disposed within in lumen 96 to push against end 98 of lumen 96 thereby extending or stretching the pleated distal portion 94 relative to the opposing wall portion 96, again resulting in the same differential tension and curvature of the instrument tip. In the case where a single lumen 96 and push wire is insufficient to provide enough differential tension across the cross section of instrument 16, a plurality of such lumens may be employed in parallel all on one half circle of the instrument cross section. Similarly, instead of a push wire, a pull wire may be employed so that lumen 96 compressed along its pleated section in the situation where the pull wire is attached to end 98 such as to a small compression plate which may be embedded in wall 84. In the foregoing, lumen 96 need not be assumed to be circular in cross section, but may be free form in its cross-sectional shape assuming instead the arcuate cross section depicted in FIG. 14 to thereby accommodate substantially greater extendibility or compressibility of the pleated section. Similarly, the push wire or pull wire disposed therein may have a similarly conforming or space-filling shape to act in the manner of a stylet internal to wall 84 and thereby to be more conveniently handled as a single piece rather than as a plurality of small circular wires.

Figure 15:
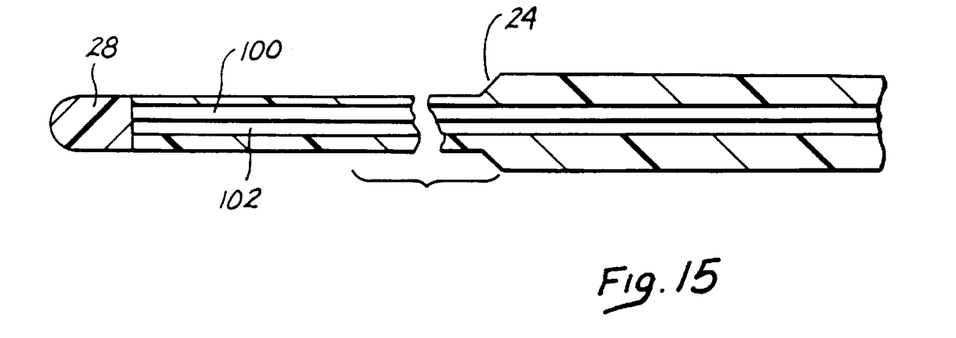
FIG. 15 is a simplified longitudinal cross sectional view of the distal portion of still another instrument according to the invention.

FIG. 15 illustrates another embodiment in which the differential tension or compression used to curve or steer the elongated instrument is created by a pressurizable longitudinal lumen 100 defined in instrument 16 and an opposing tensile nonmetallic filament 102 embedded into instrument 16 or disposed in another lumen. For example, filament 102 may be a Dacron or substantial nonstretchable filament disposed off-center in a lumen and attached at its distal end to tip 28 or an adjacent tip portion. Tension applied to filament 102 will therefore cause the tip of instrument 16 to curve back on itself. In the case where instrument 16 is very flexible and does not have sufficient resiliency in its walls to restraighten itself after the tension is removed, as is the case with a pacemaker lead, lumen 100 is pressurized with saline causing instrument 16 to temporarily assume a rigid straight configuration. After the fluid pressure is removed, instrument 16 then reassumes its limp, flexible and undefined shape. In one embodiment filament 102 may in fact be disposed in lumen 100, which is then is defined in instrument 16 in an off or on axis position as may be desired.

Alternatively, lumen 100 can be made telescopic by an accordion construction or inherent resiliency or both, and filament 102 disposed therein to apply a tensile force to compress or bend lumen 100 back on itself. Filament 102 could also be disposed in a parallel offset lumen of its own and brought around a direction changing pulley-like distal bend (not shown) and attached to the distal end of lumen 100 to apply a stretching force on lumen 100, which would tend to straighten it or even to pull itself over on itself in a bend. In such an embodiment the inflation of lumen 100 would become unnecessary, since it would be established by tension on filament 102. Pairs of such filaments 102 could then be employed, one filament disposed in or near lumen 100 and arranged to compress lumen 100 by a tensile force from that filament, and the other filament disposed in an opposing parallel lumen and arranged to stretch lumen 100 by a tensile force from that other filament. The tip of the instrument could then be pulled back on itself to form a curve or straightened out by pulling on either one of the two filaments to control the tip like a marionette.

Figure 18:
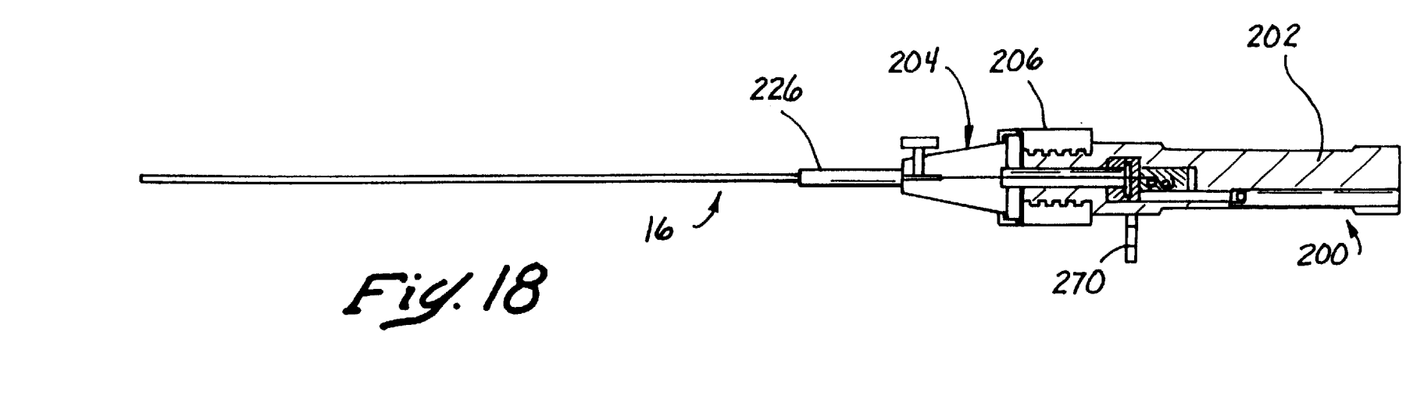
FIG. 18 is a side cross-sectional view of a handle of FIG. 16 in reduced scale showing the handle and stylet coupled and adjusted so that there is no appreciable curvature in the stylet.
Figure 19:
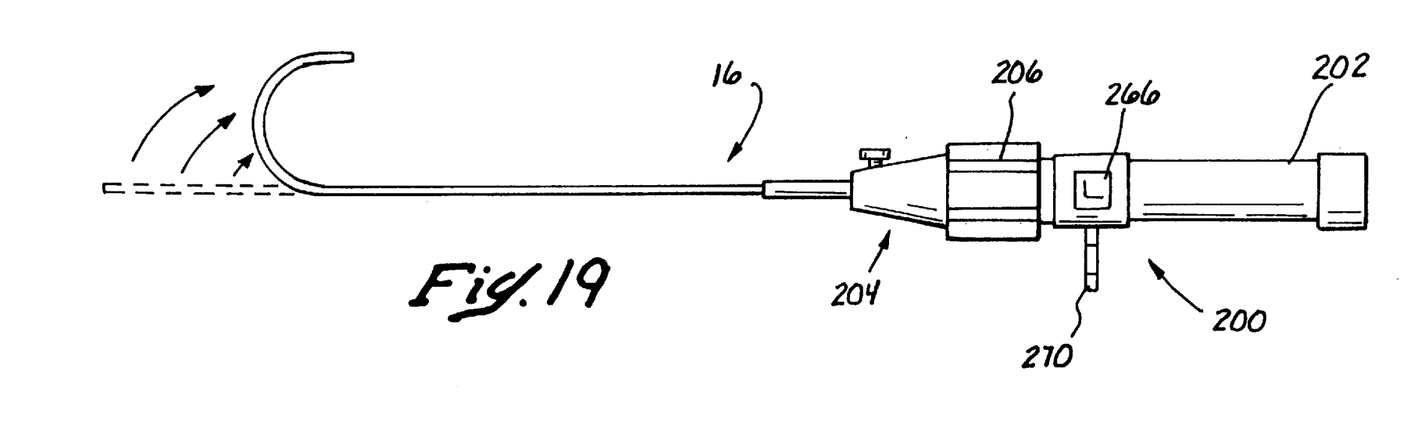
FIG. 19 is a side cross-sectional view of a handle of FIG. 16 similar to FIG. 18 showing the handle and stylet coupled and adjusted so that there is a curvature in the stylet.
Figures 20, 21:
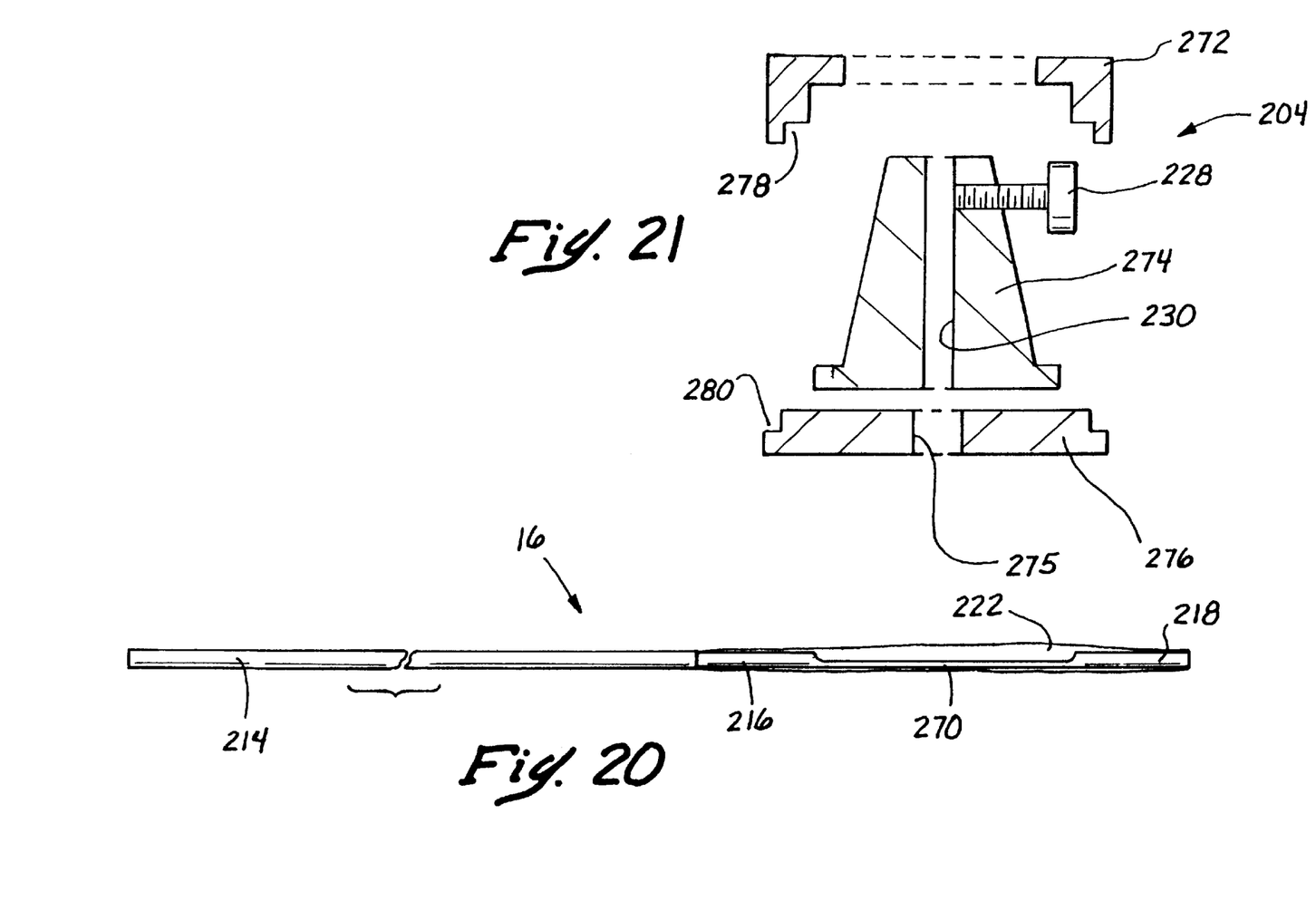
FIG. 20 is a side elevational view of the hollow tube of the stylet showing the reduced diameter portions and polymeric jacket thereon.
FIG. 21 is an exploded side cross-sectional view of the rotatable tip of the handle of FIGS. 16, 18 and 19 showing its three-piece construction.

Consider now handle 200 of FIGS. 16–19 and 21, which in the illustrated embodiment is used with the stylet of FIG. 20. It must be expressly understood that handle 200 can be used with any tensioned stylet as taught by the invention in addition to the one specifically described in FIG. 20. In the illustrated embodiment stylet 16 as shown in FIG. 20 is comprised of an outer hollow metal tube 214 which is disposed inside of a lumen of a catheter (not shown) into which stylet 16 is asserted. Hollow metal tube 214 has two reduced diameter sections 216 and 218 on its distal portions 216 and 218 and a cutaway portion 220 between distal portions 216 and 218. For example, in the embodiment wherein hollow metal tube 214 has an outer diameter of 0.0160 inch, portions 216 and 218 have been turned down to have an outer diameter of approximately 0.013–0.0135 inch. Cutaway portion 220 also has the same outer diameter of portions 216 and 218, but additionally has been ground away on one side or radius so that it has a side elevational view thickness of approximately 0.008–0.0085 inch. Wire 18 is then disposed in the axial lumen within hollow tube 214 along its length through reduced portion 216, cutaway portion 220 and into the distal reduced portion 218 wherein it is fixed or welded. The inner diameter of the lumen is approximately 0.0075 inch so that the lumen is opened in portion 220.

A flexible plastic or polymeric jacket 220 is disposed over portions 216, 218 and 220 bringing the overall outside diameter of those portions including jacket 222 back to or near the diameter of hollow tube 214 and also closing the lumen in tube 214 while still allowing wire 18 a certain degree of radial movement in portion 220 beyond the strict confines of the lumen diameter. This is believed to assist in curving the distal end of stylet 16. The reduced diameter of portions 216, 218 and 220 tend to confined the bending of stylet 16 to portions 216, 218 and 220 and in particular providing the highest curvature in portion 220. The addition of jacket 222 serves to add resiliency to portions 216, 218 and 220 and to prevent kinking of stylet 16 or catastrophic inelastic failure of the distal tip under radial load.

Figure 16:
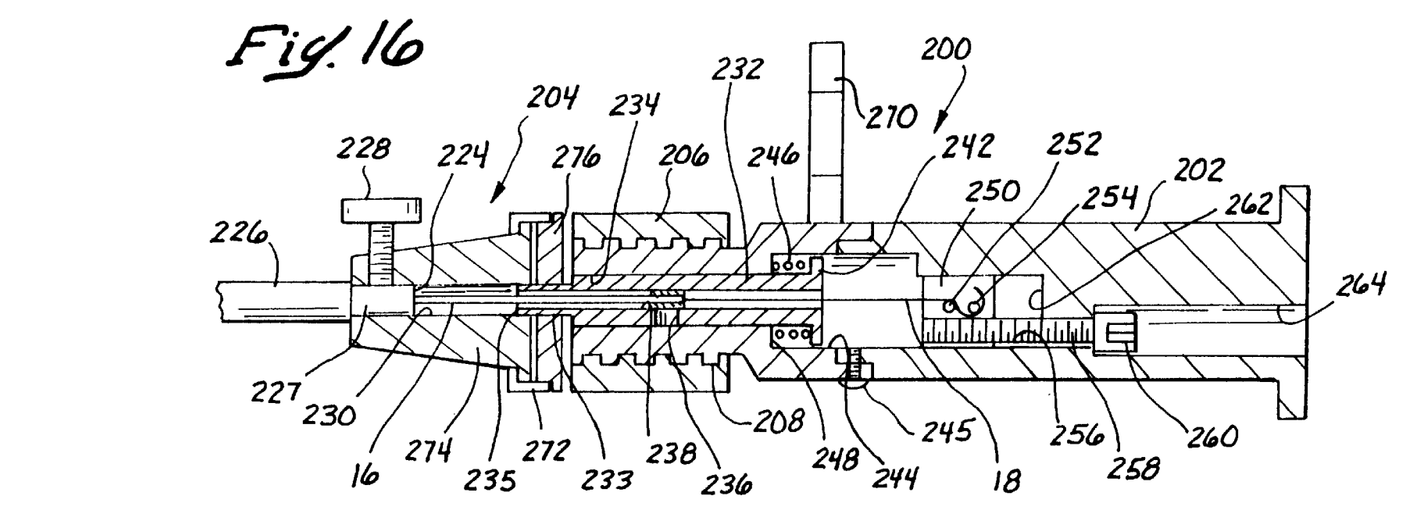
FIG. 16 is a side cross-sectional view of a handle for manipulating one embodiment of the invention in which the stylet uses a tension wire in a hollow core tube.
Figure 17:
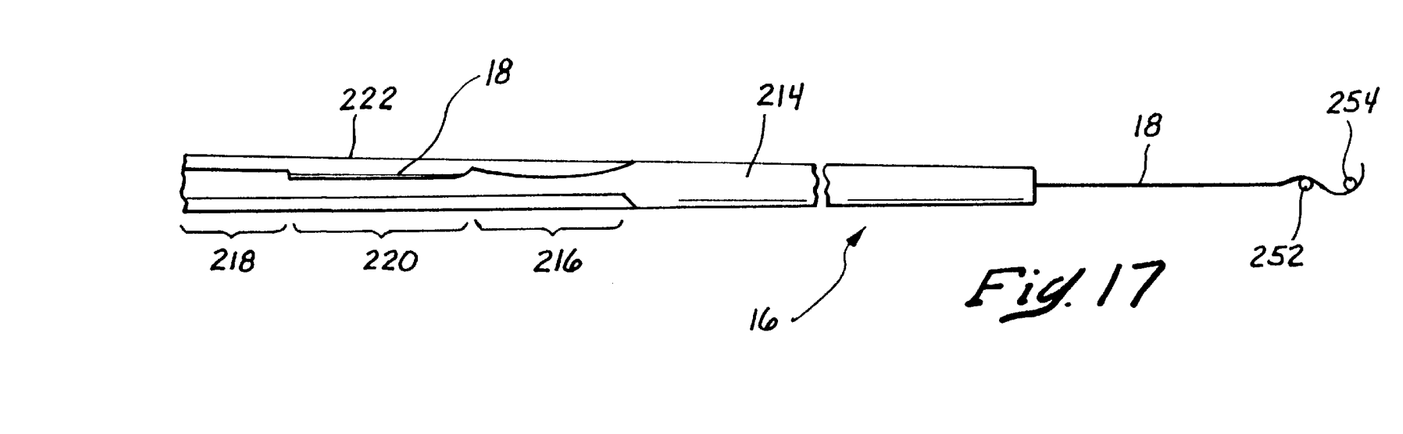
FIG. 17 is a schematic diagram of the tube, wire and a pair of pins included in the handle of FIG. 16.

Handle 200 in FIG. 16 is comprised of a two-part handle body 202 fitted to a distal conical tip 204. Tip 204 is shown in enlarged scale in exploded view in FIG. 21 and is comprised of a capturing tire 272, a cone 274 and a cap 276. Cap 276 to fixed or glued end 233 of a keyed sleeve 232 described below. Tire 272 is disposed over cone 274 and glued on its lower peripheral shoulder 278 to flange 280 of cap 276. Cone 274 is captured between tire 272 and cap 276 and is free to rotate with respect to both tire 272 and cap 276. Set screw 228 is provided through the distal portion of cone 274 to clamp to the terminal pin of catheter 226. Thus, tip 204 is retained on body 202 by means of the fixation of tire 272 to cap 276, which in turn is fixed to keyed sleeve 232. A nut 206 engaged with threads 208 formed on the distal end of handle body 202. Nut 206 rotates freely with respect to cap 276 and bears against cap 276 to thereby draw distal end of handle body 202 toward or to push distal end of handle body 202 away from cap 276 as nut 206 is rotated and handle body 202 maintained rotational fixed in the surgeon's hand.

Catheter 226 has a terminal pin 227. Pin 227 is disposed into an axial lumen 230 of tip 204 and secured in the distal end of tip 204 by means of a thumb or set screw 228. Stylet 16 extends out of terminal pin 227 and continues through lumen 230 in cone 274 and hole 275 defined in cap 276 as best seen in FIG. 21. As described below, stylet 16 is disposed into an axial lumen 238 in sleeve 232 and hallow tube 214 is epoxied to sleeve 232 through epoxy access hole 236.

Conical tip 204 serves to minimize the stress on stylet 16, which is very thin and easy to kink. Handle 200 is comparatively heavy compared to stylet 16 and its use could easily kink stylet 16. Tip 204 provides additional support to stylet 16 where they join with handle body 202 and provide for a more flexible and widely distributed stress over the region of their common coupling.

As just stated stylet 16 then continues from end 224 of terminal pin 227 of catheter 226 through the axial lumen 230 in tip 204 and into an axial lumen 238 disposed through a square keyed sleeve 232. Hallow tube 214 but not wire 18 is then fixed to square keyed sleeve 232 by means of an epoxy supplied through hole 236 transversely defined into keyed sleeve 232 and extending to longitudinal lumen 238 defined therethrough. Squared keyed sleeve 232 is disposed in a conforming square hole 240 defined through the distal end of handle 202. The proximal end of keyed sleeve 232 is provided with a flange head 242 and is disposed in a cavity 244 defined in handle 202. Cavity 244 is formed from the two halves of handle body 202 which are slip fit together and secured by one or more radial screws 245.

A compression spring 246 is captured between flange head 242 and the distal surface 248 of cavity 244. The opposing distal end 233 of sleeve 232 is epoxied into hole 275 of cap 276. In this manner rotation of tip 204 relative to handle body 202 is allowed with it is positively retained on handle body 202.

Wire 18 continues from epoxy hole 236 into a slide block 250 which carries two transverse pins 252 and 254 around which wire 18 is wrapped. The diameter of transverse pins 252 and 254 is chosen to be large enough to prevent bending or fatiguing of wire 18 to such a degree that when under repeated tension wire 18 breaks. For example, if wire 18 has a diameter of 0.007–0.008 and is made of stainless steel, a diameter of 0.080 for transverse pins 252 and 254 is sufficient to avoid breakage under the tensile loads encountered in the invention.

Slide block 250 is threadably coupled to an adjustment screw 256. Adjustment screw 256 extends through a smooth bore 258 and into a slide block cavity 262 defined into the proximal handle body half into which slide block 250 is slidingly disposed. Adjustment screw 256 is provided with a socket head 260 which in turn is disposed in a clearance hole 264 which extends through the proximal length of handle body 202 to provide access by means of an Allen wrench or other similar tool to socket head 260.

The elements of handle of 200 as shown in cross-sectional view FIG. 16 and stylet at 16 as shown in side elevational view in FIG. 20 now having been described, the operation of the combination of handle 200 and stylet 16 can be understood. Wire 18 disposed within hollow tube 214 and welded to hollow tube 214 at its distal tip, is fixed at its proximal end to pins 252 and/or 254 of slide block 250. This is schematically illustrated in the side elevational view of FIG. 17 which shows the elements of stylet 16 in isolation from the remaining elements of handle 200 and catheter 226 except for pins 252 and 254. Wire 18 is thus fixed to handle body 202 by means of attachment through pins 252 and 254 to slide block 250.

Nut 206, which may include a knurled surface treatment to facilitate manual gripping, is then rotated. Handle body 202 is held stationary by the surgeon and does not rotate. Keyed sleeve 232 is fixed to hallow tube 214 and hence prevents the rotation of hallow tube 214. As nut 206 is rotated, handle body 202 is backed out of nut 206 by threads 208. This causes wire 18 to be drawn out of hollow tube 214 thereby changing the configuration of stylet 16 from the straight untensioned configuration as shown in FIG. 18 to the curved configuration shown in FIG. 19 by reason of localization of the bending in distal portions 216, 218 and 220 of hollow tube 214 and in a particular ground portion 220. Polymer jacket 222 assists in the resiliency of portions 216, 218 and 220 along with the inherent resiliency of hollow tube 214 to return distal portions 216, 218 and 220 to a straight configuration after the tension on wire 18 is removed.

As wire 18 is withdrawn from hollow tube 214, the tension on it increases. The greater the withdrawal, the greater the degree of tension. This tension is applied to keyed sleeve 232 to cause compression spring 246 to be compressed. Adjustment screw 258 coupled to slide block 250 is sufficiently backed off to allow sleeve 232 to advance or be drawn into bore 234 without socket head 260 bottoming out on bore 264. Ultimately, flanged head 242 will completely compress spring 246 to its maximum extent and/or bear against distal wall 248 of cavity 244. This provides a mechanical stop to the degree of withdrawal of wire 18 from hollow tube 214 and hence a mechanical stop which limits the degree of curvature of the distal end of stylet 16. Adjustment screw 258 can then be tightened to draw slide block 250 further back or proximally into cavity 262. This will increase the tension on wire 18 and cause even further bending of stylet 16 as shown in FIG. 19.

When nut 206 is reversed, body 202 is again effectively drawn into threads 208 of nut 206 reducing tension on wire 18 and allowing stylet 16 to straighten. Adjustment screw 258 may also need to be reversed in order to completely straighten stylet 16 as shown in FIG. 18 depending on what prior adjustments have been made.

Indicator 266 as shown in FIG. 19 is an engraving provided on the outside of handle body 202 in the shape of a J which serves as an indicator to the surgeon of the direction which the distal tip of stylet 16 will curve when nut 206 is rotated. Note that hollow tube 214 is fixed to sleeve 232 which in turn is rotationally fixed to handle body 202. Thus, tube 214 is carefully oriented when inserted into tip 204 before fixing with set screw 228 to insure that indicator 266 is accurately corrected to the actual direction of bending before use.

The free rotatability of cone 274 allows handle 200 of the invention to be beneficially combined with a conventional active fixation pacemaker lead in the place of catheter 226. Note that cone 274 rotates freely in either direction between tire 272 and cap 276. Nut 206 serves to draw in or push out body 202 of handle 200, but it does not tighten down on tip 204. This allows tip 204 to be manually rotated by means of the use of set screw 228 as a lever, if desired, and hence to rotate terminal pin 227 of catheter 226 which is clamped to tip 204 by set screw 228. When set screw 228 is applied or locked to terminal pin 227 of a conventional active fixation pacemaker lead, which has a heart attachment fixture on its distal end, rotation of tip 204 activates or advances a screw-extrusion mechanism allowing the distal end of the attached lead to become fixed to the heart tissue. Similarly, reversed rotation of tip 204 will allow the active fixation pacemaker lead to be unscrewed or retracted from the heart tissue. Note that rotation of cone 274 does not cause stylet 16 to be rotated, which is allowed to rotate within its lumen in catheter 226. Cone 274 is not rotationally fixed to sleeve 232 and hence is not rotationally fixed to stylet 16.

The ease of use of handle 200 is enhanced by the addition of an attachment ring 270 to handle 200 shown in FIG. 19 so that it can be attached by a conventional sheet clamp to the field of operation and its position stabilized. Ring 270 may be connected to any point on handle 200 desired, but the preferred point of connection to at or near the center of mass of handle 200 so that it is balanced when hanging from its attachment through ring 270.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A handle and deflectable stylet for disposition into a catheter comprising:
   a non-rotational handle body; and
   a rotatable adjustment coupled to said handle body, said handle body being coupled to a deflectable stylet and adapted to apply a tension thereto to cause said stylet to deflect according to the degree of rotation of said adjustment relative to said non-rotational handle body,
   wherein said catheter has a terminal pin and wherein said handle body is further combined with a rotatable tip, said stylet being disposed through said tip such that said stylet is coupled to and rotationally fixed with respect to said handle body, said tip being rotationally free with respect to said handle body and selectively rotationally fixed to said terminal pin of said catheter.

2. The handle of claim 1 when said rotatable adjustment is a nut threadably coupled to said handle body, said tip being coupled to and captured by a rotationally free engagement with said handle body.

3. The handle and stylet of claim 2 wherein said stylet is comprised of a hollow tube and tension wire coupled to said hollow tube, said hollow tube being fixed to a keyed sleeve, said keyed sleeve being longitudinally slideable in and keyed to said handle body to be rotationally fixed thereto, said keyed sleeve having a mechanical stop, said wire being fixed with respect to said handle body.

4. The handle and stylet of claim 3 wherein said keyed sleeve is resiliently biased relative to said handle body to apply a tension to said tension wire.

5. The handle and stylet of claim 4 further comprising a screw adjustment, said screw adjustment adjusting the relative longitudinal displacement of said keyed sleeve to said handle body to add tension to said wire.

6. The handle and stylet of claim 5 further comprising a slide block forming part of said screw adjustment, said tension wire having its distal end fixed to said slide block, said slide block being longitudinally positionable within said handle body by said screw adjustment.

7. A handle and deflectable stylet for disposition into a catheter comprising:
   a non-rotational handle body; and
   a rotatable adjustment coupled to said handle body, said handle body being coupled to a deflectable stylet and adapted to apply a tension thereto to cause said stylet to deflect according to the degree of rotation of said adjustment relative to said non-rotational handle body,
   further comprising an attachment ring connected to said handle body to permit fixation of said handle with a field of operation.

8. A handle and deflectable stylet for disposition into a catheter comprising:
   a non-rotational handle body; and
   a rotatable adjustment coupled to said handle body, said handle body being coupled to a deflectable stylet and adapted to apply a tension thereto to cause said stylet to deflect according to the degree of rotation of said adjustment relative to said non-rotational handle body,
   in further combination with said deflectable stylet, said deflectable stylet comprising a hollow tube having a distal end and a proximal end coupled to said handle, wherein said hollow tube has a central coaxial tension wire disposed therein and fixed thereto at said distal end of said tube, said hollow tube has a reduced diameter section through which said central coaxial tension wire is disposed, a portion of said reduced diameter section being removed to form a flexure section, said hollow tube having a distal portion in which said central coaxial tension wire is fixed, said distal portion having a full diameter and not being included within said flexure section.

9. The handle and stylet of claim 8 further comprising flexible hollow cylindrical sleeve of uniform diameter, said sleeve being concentrically disposed over said flexure section of said hollow tube to prevent kinking of said flexure section.

10. The handle and stylet of claim 9 wherein said hollow tube has an outer diameter and wherein said flexible sleeve is plastic tubing having an inner diameter adapted to snugly fit over said reduced diameter section and an outer diameter comparable to said outer diameter of said hollow tube.

11. A handle and deflectable stylet disposable within a lumen in a catheter, which stylet and catheter is curved upon application of tension to a tension wire disposed in said stylet and extending from its proximal end to its distal end wherein said tension wire is fixed, said handle comprising:
   a non-rotatable body adapted to be held by a user; and
   a screw micrometer telescopic adjustment for moving said non-rotatable body longitudinally relative to a catheter, said non-rotatable body being coupled to a tension wire so that said tension wire is drawn out of a deflectable stylet and tension applied to said tension wire to thereby curve said stylet and hence to curve said catheter.

12. The handle and stylet of claim 11 wherein said telescopic adjustment is a rotatable collar which longitudinally displaces a first portion of said body coupled to said tension wire from a second portion of said body coupled to said stylet.

13. The handle and stylet of claim 12 further comprising a keyed sleeve coupled to said stylet and rotationally fixed but slideable in said first portion of said body coupled to said tension wire so that said first and second portions of said body are rotationally fixed with respect to each other while remaining longitudinally displaceable by action of said telescopic adjustment.

14. The handle and stylet of claim 12 further comprising a stop to prevent longitudinal displacement of said first and second portions of said body beyond a predetermined distance.

15. The handle and stylet of claim 12 further comprising a stop to prevent curvature of said distal portion of said stylet beyond a predetermined flexure.

16. The handle and stylet of claim 12 wherein said telescopic adjustment is by means of rotation of a tensioning member which translates rotation of said member into tension on said wire.

17. The handle and stylet of claim 14 further comprising a screw adjustment to add tension to said wire after said stop has been first actuated..

18. The handle and stylet of claim 11 wherein said telescopic adjustment is by means of rotation of screw micrometer which reversibly tensions said wire.

19. The handle and stylet of claim 11 further comprising a tip, said stylet being disposed through a lumen in said tip, said catheter being coupled to said tip so that said tip provides stress relief to said stylet when said handle is coupled to said catheter.

20. The handle and stylet of claim 19 where said tip is longitudinally coupled to said body, but rotationally free with respect to said body.

21. The handle and stylet of claim 20 in further combination with a terminal pin of said catheter, wherein said catheter is an active fixation pacemaker lead, and further comprising a screw lock disposed in said tip to lock said terminal pin so that said terminal pin rotates with said tip to activate fixation of said catheter.

* * * * *